United States Patent

Maitra et al.

Patent Number: 5,874,111
Date of Patent: Feb. 23, 1999

[54] PROCESS FOR THE PREPARATION OF HIGHLY MONODISPERSED POLYMERIC HYDROPHILIC NANOPARTICLES

[76] Inventors: Amarnath Maitra, D-2 University Flats, 8 Cavalry La., Delhi-110007; Prashant Kumar Ghosh, Block C2B, Flat 5A, Janakpuri, New Delhi-110058; Tapas K. De, TC-18, Gwyer Hall, University Marg, Delhi-110007; Sanjeeb Kumar Sahoo, DC-14A, Gwyer Hall, University of Delhi, Delhi-7, all of India

[21] Appl. No.: 779,904
[22] Filed: Jan. 7, 1997
[51] Int. Cl.[6] .............. A61K 9/51; A61K 47/32; B01J 13/20
[52] U.S. Cl. .......... 424/499; 424/501; 528/481; 528/482; 528/488
[58] Field of Search ............ 424/501, 909, 424/499

[56] References Cited

U.S. PATENT DOCUMENTS

| | | | |
|---|---|---|---|
| 4,105,598 | 8/1978 | Yen et al. | 526/909 |
| 4,329,332 | 5/1982 | Couvreur et al. | 424/501 |
| 4,438,239 | 3/1984 | Rembaum et al. | 424/501 |
| 4,741,872 | 5/1988 | De Luca et al. | 424/501 |
| 4,871,716 | 10/1989 | Longo et al. | 424/501 |
| 5,183,879 | 2/1993 | Yuash et al. | 526/909 |
| 5,508,313 | 4/1996 | Delgado et al. | 526/909 |

*Primary Examiner*—Peter F. Kulkosky
*Attorney, Agent, or Firm*—Spencer & Frank

[57] ABSTRACT

Preparation of highly monodispersed polymeric hydrophilic nanoparticles having a size of up to 100 nm (in which may have drug substances encapsulated therein. The process comprises subjecting a mixture of an aqueous solution of a monomer or preformed polymer reverse micelles, a cross linking agent, initiator, and optionally, a drug or target substance to polymerization. The polymerized reaction product is dried for removal of solvent to obtain dried nanoparticles and surfactant employed in the process of preparing reverse micelles. The dry mass is dispersed in aqueous buffer and the surfactant and other toxic material are removed therefrom.

14 Claims, 5 Drawing Sheets

PROCESS FOR THE PREPARATION OF HIGHLY MONODISPERSED POLYMERIC HYDROPHILIC NANOPARTICLES

BACKGROUND OF THE INVENTION

1. Field of the Invention

This invention relates to a process for the preparation of highly monodispersed polymeric hydrophilic nanoparticles with or without target molecules encapsulated therein and having sizes of up to 100 nm and a high monodispersity.

2. Description of the Related Art

Following an administration of a drug in a living system the active substance is distributed throughout the body as a function of its physicochemical properties and molecular structure. The final amount of drug reaching its target site may only be a small fraction of the administered dose. Accumulation of drug at the non-targeted site may lead to adverse effect and undesirable side reactions. Therefore, targeting of drug to specific body sites is necessary.

One way of modifying the biodistribution of drugs in the body is to entrap them in ultrafine drug carriers. Among these carriers, liposomes, nanoparticles and pharmacosomes have been extensively studied. The use of liposomes as drug targeting agents is found to be limited due mainly to the problems of low entrapment efficiency, drug instability, rapid drug leakage and poor storage stability. With the aim of overcoming these problems, the production of polymeric nanoparticles has been investigated since the last two decades. Nanoparticles are defined as solid colloidal particles ranging in size from about 10 nm to 1000 nm.

A large number of studies have been reported on recent advances in drug targeting possibilities and sustain release action with nanoparticles encapsulating drugs. In vivo studies have also been reported with special attention to the reticuloendothelial system (RES). Some in vivo studies concerning nanoparticles administration by oral and ocular routes have also been reported in the literature with respect to the possible improvements of bioavailability. These polymeric nanoparticles should be non antigenic, biocompatible and biodegradable.

Figure 1:
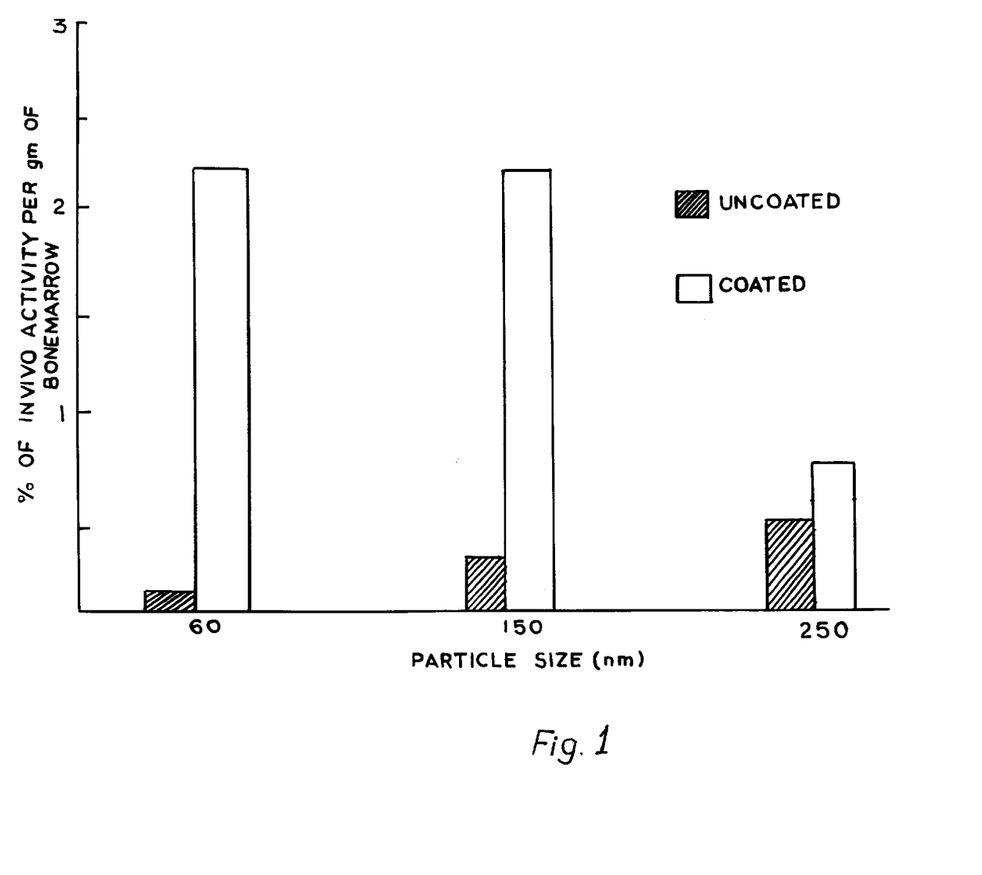
FIG. 1 shows size dependent uptake of nanoparticles, uncoated and coated with poloxamer surfactant by bone marrow.

The important characteristics of the particles used for targeting at specific body sites were found to be influenced mainly by two factors: (i) the size of the nanoparticles and (ii) the surface characteristics of the nanoparticles. Particles smaller than 7 $\mu$m and specially nanoparticles are not filtered in the lung and their biodistribution is dependent on their interaction with reticuloendothelial system (RES). Biodegradable nanoparticles are mainly taken up by the Kupffer cells in the liver while small amount of these particles go to macrophages in spleen and bone marrow. Bone marrow uptake and targeting at other sites can be modified drastically by reducing the particle size. Nanoparticles of 200 nm diameter and above have biodistribution dependent on their interaction with RES. The distribution, however, can be reversed if the particle size is made much smaller (i.e. below 100 nm) and particle surfaces are made hydrophilic. As an example, it has been found that if these particles are separated into three size ranges –60 nm, 150 nm and 250 nm and their surfaces are rendered hydrophilic by adsorbing poloxamer type of surfactants, then the small sized particles with maximum surface hydrophilicity are mostly taken up by cells other than Kupffer cells and as shown in FIG. 1 of the accompanying drawings. Specifically FIG. 1 shows size dependant uptake of nanoparticles, uncoated and coated with poloxamer surfactant by bone marrow. These small particles in the blood serum do not adsorb serum protein through opsonisation and as a result, their circulation time in blood is considerably increased. Hydrophobic particles are removed from the circulation very rapidly due to opsonisation. Nanometer sized particles with hydrophilic surface remain in blood for longer period of time so that targeting at specific sites may be facilitated.

At present, nanoparticles for drug encapsulation are prepared by methods involving either polymerisation of dispersed monomers or a dispersion of preformed polymers in emulsion in presence of desired drug. The methods known in the art for the preparation of nanoparticles are (i) dispersion polymerisation method, (ii) emulsion polymerisation method, (iii) dispersion of synthetic polymer nanospheres in emulsion, and (iv) interfacial polymerisation technique. In all these methods emulsions of oil-in-water are used and the polymer is formed or dissolved in the oil phase. As a result, the polymeric materials are always hydrophobic because they are to be soluble in oil and the particles formed are nanoparticles of larger size (i.e., above 100 nm) because the average size of the emulsion droplets is mostly 100 nm and above diameter. More over, since the emulsion droplets are highly polydispersed, the nanoparticles formed have broad spectrum size range and these are also highly polydispersed. Thus, in such known processes (i) one cannot prepare nanoparticles of subcolloidal size and (ii) the emulsion medium demands that the polymeric materials should be hydrophobic.

SUMMARY OF THE INVENTION

An object of this invention is to propose a novel process for the preparation of highly monodispersed polymeric nanoparticles with or without targeted materials and having a size of up to 100 nm with a high monodispersity.

A further object of this invention is to propose a process for the preparation of said polymeric nanoparticles capable of being modulated to required sizes.

Another object of this invention is to propose a process for the preparation of said highly monodispersed polymeric nanoparticles of subcolloidal size with or without targeted materials.

Still another object of this invention is to propose a process for the preparation of said hydrophilic polymeric nanoparticles.

A further object of this invention is to propose a process for the preparation of said highly monodispersed drug loaded polymeric nanoparticles dispersed in aqueous buffer and free of any toxic material.

A still further object of this invention is to propose a process for the preparation of highly monodispersed drug loaded polymeric nanoparticles of hydrophillic in nature which obviates the disadvantages associated with these of the prior art.

Yet another object of this invention is to prepare a process for the insertion and loading of target drug/target substance in nanoparticles to secure them from outer intervention in vivo or cell culture invitro till they are exposed at the target site within the cell.

BRIEF DESCRIPTION OF THE DRAWINGS

FIG. (3b) shows nanoparticles made of polyvinylpyrrolidone containing FITC-Dextran.

DETAILED DESCRIPTION OF THE INVENTION

According to this invention there is provided a process for the preparation of highly monodispersed polymeric hydrophillic nanoparticles with or without targeted materials having a size of up to 100 nm with a high monodispersity comprising in the steps of:

(i) dissolving a surfactant in oil to obtain reverse micelles;

(ii) adding an aqueous solution of a monomer or preformed polymer to said reverse micelles and a crosslinking agent, initiator and drug or a target substance, if required;

(iii) subjecting such a mixture to the step of polymerization;

(iv) drying the polymerized reaction product for removal of solvent to obtain dry nanoparticles and surfactant;

(v) dispersing the dry mass in aqueous buffer; and (vi) separating the surfactant and other toxic materials therefrom.

In accordance with this invention, the aqueous core of a reverse micellar droplet is used as a nanoreactor for the preparation of nanoparticles. The sizes of the aqueous core of such droplets are in the range of 1 nm–10 nm. The size of the particles which are formed primarily inside these droplets are larger than the size of the aqueous core of the droplets. Moreover, since the polymerisation takes place in an aqueous medium, polymers with surface hydrophilic properties are obtained by this invention. Therefore, using reverse micellar method of the present invention, it is possible to prepare very small size nanoparticles with hydrophilic surface so that their opsonisation as well as uptake by RES is substantially minimized. High mono-dispersity of the particles is possible because reverse micellar droplets in which the polymeric reactions are carried out are highly monodispersed.

The aqueous phase is regulated in such a manner so as to keep the entire mixture in an optically transparent micro emulsion phase. The range of the aqueous phrase cannot be defined as this would depend on factors such as the monomer, surfactant or polarity of oil, and the only factor is that the system is in an optically transparent micro emulsion phase.

In accordance with the present invention, the nanoparticles have a size range of up to 100 nm, preferably a size of up to 10 nm to 100 nm.

In accordance with this invention the aqueous core of a reverse micellar droplet is effectively used as nanoreactor to prepare ultrafine nanoparticles and to encapsulate the drugs (normally water soluble chemicals of maximum size up to that of 100–200 k Dalton protein. By the process of the present invention, extremely small particles of size of greater uniformity and down to about 10 nm diameter has been achieved.

The surfactant, sodium bis ethylhexylsulphosuccinate, or AerosolOT (i.e., AOT) is dissolved in n-hexane to prepare reverse micelles. To the AOT solution in hexane (usually 0.03M to 0.1M of AOT in hexane), aqueous solutions of monomer or preformed polymer, crosslinking agent, initiator and drug are added and the polymerisation is done in presence of nitrogen gas. Additional amount of water may be added in order to get nanoparticles of larger size. The maximum amount of drug that can be dissolved in reverse micelles varies from drug to drug and has to be determined by gradually increasing the amount of drug till the clear microemulsion is transformed into translucent solution. All the stock solutions are prepared in phosphate buffer and the contents swirled vigorously in order to ensure the transparency of the solution. The reaction mixture is purged with nitrogen gas. Polymerisation is done in nitrogen atmosphere. The solvent n-Hexane is then evaporated out at a temperature, for example, of 35° C. using rotary evaporator under low pressure when transparent dry mass is obtained. The material is dispersed in water and to it CaCl2 solution is added drop by drop till all the calcium salt of diethylhexylsulphosuccinate (Ca(DEHSS)2 from AOT) is precipitated. The mixture is then subjected to centrifugation, for example, at 15000 rpm for 10 mins. The supernatant is decanted off which contains nanoparticles containing encapsulated drug. Some nanoparticles remain absorbed in the cake of the precipitate. For complete recovery of the nanoparticles from the precipitated calcium (DEHSS)2 the latter is dissolved in n-hexane and the nanoparticles extracted with water. The aqueous dispersion is immediately dialysed through, for example, 12,000 cut off dialysis membrane for about one hour and the liquid lyophilised to dry powder and stored at low temperature till further use.

Figure 2:
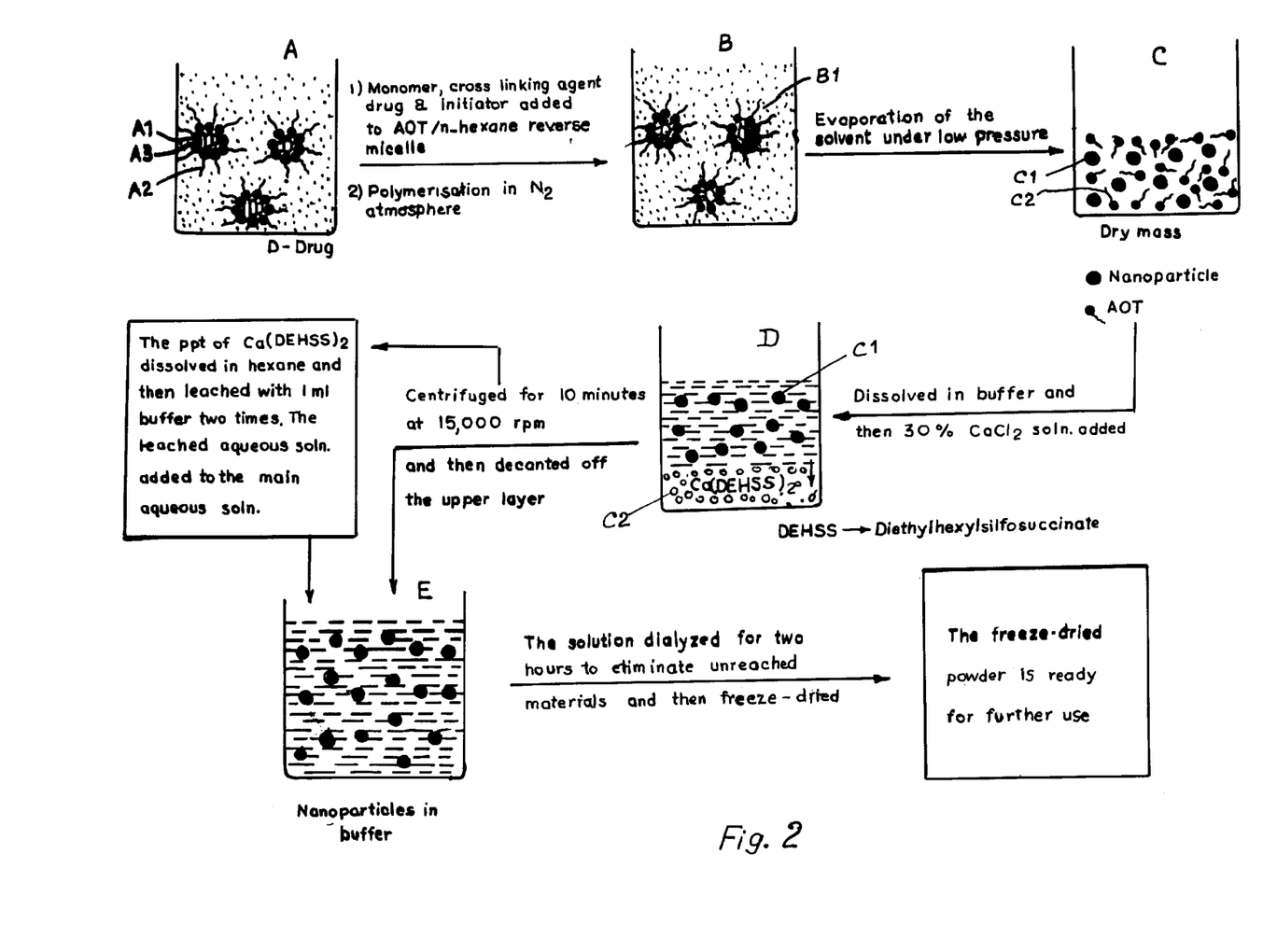
FIG. 2 illustrates the flow diagram for the preparation of nanoparticles using a microemulsion.

Reference is now made to FIG. 2 of the accompanying drawings which illustrates the flow diagram for the preparation of nanoparticles using microemulsion. Step A shows a reverse micellar droplet A1, prepared by dissolving the surfactant in oil. Thus, when a surfactant is dissolved in oil, then the hydrophobic constituent tails A2 would remain in contact with oil and an inner core A3 would comprise of hydrophillic constituents. When water is added to a solution containing reverse micelle A1, of as the hydrophillic constituent is soluble in water, water is attracted to the hydrophillic domain or core A3. A monomer, crosslinking agent, the required drug and initiator is added to the reverse micelle A1. As the aforesaid constituents are hydrophillic in nature, such constituents go to the core A3. Polymerization is carried out in nitrogen atmosphere to form a polymer B1 and encapsulated drug as shown in step B. In step B, an evaporation is effected under low pressure for removal of the solvent. Step C illustrates the dried mass to consist of Nanoparticles C1, and surfactant C2. The dried mass is dissolved in phosphate buffer and then 30% CaCl2 added thereto drop by drop in step D to precipitate the surfactant as calcium-diethylhexylsulfosuccinate (DEHSS). Step D illustrates the nanoparticles C1 and calcium DEHSS. The solution of step D is centrifuged at step E to obtain clear nanoparticles dispersed in buffer and the precipitate of Ca(DEHSS)2.

The cake of Ca(DEHSS)2 may contain some absorbed nanoparticles which can be recovered by dissolving the cake in hexane and leaching the nanoparticles by buffer 2 to 3 times. The leaching solutions are collected along with solution E. Such a buffer solution containing nanoparticles may still contain certain unreacted or toxic materials which are removed by dialyzing the solution for two hours and then freeze dried.

Normally 0.01 to 0.1M AOT in n-hexane is used. Vinylpyrrolidone (VP) or mixture of vinylpyrrolidone and polyethyleneglycolfumarate (PEGF) are used as monomers as they form water soluble hydrogels on polymerisation and are highly biocompatible. Another suitable but antigenic polymer which as been used is bovine serum albumin. Other suitable water soluble hydrogels and biocompatible materials can be used for nanoparticle formation. In case of hydrogels, the crosslinking is done with N,N methylene bis acrylamide (MBA) whereas albumin is crosslinked by glutaraldehyde. In case of polyvinylpyrrolidone (PVP) crosslinked with MBA, the amount of monomer used is, for example, about 50 w % of AOT, and the amount of crosslinking agent (MBA) used is 1.2% w/w of the polymer. Such a composition has maximum shelf life and retention of drug by nanoparticles of this composition is also maximum. Loading of drug should be between 1% to 10% w/w of the polymer according to the solubility of the drug in the micellar system but it can also be increased if to the solubility of the drug in reverse micelles is high.

EXAMPLES

The following examples are given by way of illustration of the present invention and should not be construed to limit the scope of the present invention.

Example-I

Preparation of an antigen loaded polyvinylpyrrolidone nanoparticles

An antigen, from *Aspergilus fumigatus*, has been used as a drug for encapsulation. In a 40 ml of 0.03M AOT solution in hexane, 140 ul of freshly distilled pure vinylpyrrolidone, 35 ul of N,N'methylene bis arylamide (0.49 mg/ml), 20 ul of 1% ferrous ammonium sulphate solution, 40 ul of 11.2% aqueous solution of tetramethylethylenediamine (TMED), 10 ul of 5% potassium persulphate as initiator and 180 ul of antigen (antigen)=16 mg/ml) were added. The amount of excess buffer to be added in reverse micelles was governed by the desired size of the nanoparticles to be prepared. The volume of the excess buffer can be carried from zero to maximum amount up to which microemulsion formation is possible and no phase separation takes place. The solution was homogeneous and optically transparent. Polymerisation was done in the presence of N2 gas at 30 C. for 8 hours in a thermostatic bath with continuous stirring. The nanoparticles of polyvinylpyrrolidone containing encapsulated drug would be formed. The solvent was evaporated off in a rotary vacuum evaporator and the dry mass was resuspended in 5 ml of water. Calculated amount of 30% CaCl2 solution was added drop by drop to precipitate AOT as calcium salt bisethylhexysulphosuccinate. The centrifuged aqueous solution contains nanoparticles which was homogeneous and almost transparent. The cake of calcium DEHSS after centrifugation contains some amount of nanoparticles absorbed in it. It was dissolved in 10 ml of n-hexane and the hexane solution was washed 2–3 times each time with 1 ml water. The phase separated clear aqueous layer was drained out and was collected with the original filtrate. The total aqueous dispersion of nanoparticles was then dialysed (12,000 cut off membrane) for about 2 hours against water and the dialysed solution was lyophilised immediately to dry powder for subsequent use. The sample should be free from AOT, monomer, crosslinking agent and perdisulphate. Any trace amount of unreacted materials and surfactant could be detected through HPLC. Perdisulphate was detected chemically using starch iodide solution and the presence of AOT was tested as follows:

To an 1 mg/ml solution of dry powder, a drop of methylene blue dye was added. The solution was then mixed with 1 ml of n-hexane thoroughly and was kept for phase separation. The hexane layer was then tested spectrophotometrically at 580 nm for the presence of the dye.

Example-II

The nanoparticles from polyethyleneglycolfumarate were prepared as follows 5 g of polyethylene glycol600, 0.9 g of fumaric acid and 1.22 mg of hydroquinone were mixed together and heated at 190 C. for 7–8 hours in a 100 ml 3-necked flask equipped with a thermometer, refluxing conderser and a nitrogen inlet. The product was greenish yellow viscous liquid at room of temperature.

In a 40 ml of 0.06 m AOT in n-hexane the following components were added. 100 ul of polyethyleneglycol fumarate (0.186 g/ml) 10 ul of freshly distilled vinylpyrrolidone, 10 ul of N,N'-methylene bis acrylamide (0.049 /g/ml), 10 ul of 0.5% ferrous ammonium sulphate, 20 ul of 11.2% TMED and 10 ul or 20 ul, as the case may be, of fluorescence isothiocyanate-dextran (FITC-dextran) of mol. wt. 16 KD (160 mg/ml). 0–200 µl of buffer depending on the size of the droplet were added.

In the above solution N2 gas was passed for 30 mins and then 10 ul of 5% potassium perdisulphate was added as initiator with vigorous stirring. Thereafter, the nitrogen gas was passed through the solution for another six hours at 30 C.

The nanoparticles were recovered from the aqueous solution following the same method as described earlier in the case of polyvinylpyrrolidone particles.

Example-III

Preparation of Bovine Serum Albumin-gluteraldehyde nanoparticles

In a 40 ml of 0.06 m AOT in n-hexane 200 ul bovine serum albumin (100 mg/ml) and 0–600 ul water depending on the desired size of the micellar droplets were added. The mixture was thoroughly stirred at room temperature till a transparent microemulsion was formed. To the well stirred solution, 20 ul 5% glutaraldehyde was added and the stirring was continued for another half an hour when the nanoparticles were formed. The aqueous solution of the nanoparticles were prepared from the AOT solution following the method as described in the case of polyvinylpyrrolidone above.

The nanoparticles were characterised as follow:

The entrapment efficiency of the FITC-dextran dye in polyvinylpyrrolidone nanoparticles was determined as follows: The aqueous extract including the repeated washings were collected and was made up the volume of 10 ml. 500 µl of the solution was filtered through 100 KD membrane filter and 2 µl phosphate buffer was added. The absorbance of solution was measured at 493 nm. The absorbance of the same concentration of free FITC in phosphate buffer was measured. From the difference in absorbances the entrapment efficiency was calculated and the values as shown in the table was found to be in the range of 39–44% irrespective of the size of the nanoparticles.

| Size of the PVP particles (nm) | Entrapment Efficiency (%) |
|---|---|
| 21 | 40 |
| 26 | 44 |
| 31 | 42 |
| 34 | 40 |
| 52 | 39 |
| 96 | 40 |

The size of the nanoparticles was determined by laser light scattering measurements. Dynamic laser light scattering measurements for determining the size of the nanoparticles were performed using Brookhaven 9000 instrument with B1200SM goniometer. Argon ion air cooled laser was operated at 488 nm as a light source. The time dependence of the intensity autocorrelation function of the scattered intensity was derived by using 128 channel digital correlator. Intensity correlation data was processed by using the method of cumulants. The translational diffusion coefficient ($fT$) of the particles dispersed in aqueous buffer was obtained from a nonlinear least square fit of the correlation curve using the decay equation. From the value of the translational diffusion coefficient, the average of hydrodynamic diameter Dh of the scattering particles was calculated by Stokes-Einstein relationship $$D_h = kT/3\bar{A}\eta\, fT$$

where k is Boltzman constant, $\eta$ is the viscosity of the solvent at an absolute temperature T.

Figure 3A:
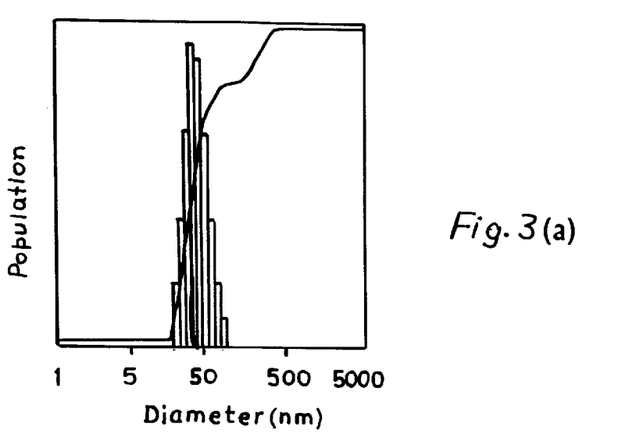
FIG. 3(a) shows nanoparticles made of polyethylene glycol fumarate containing FITC-Dextran.
Figure 3B:
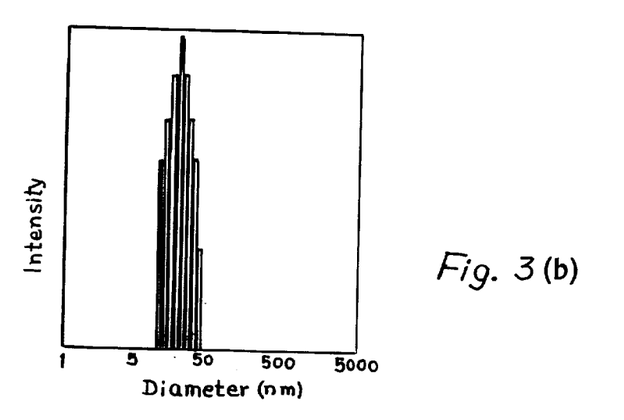
Figure 3C:
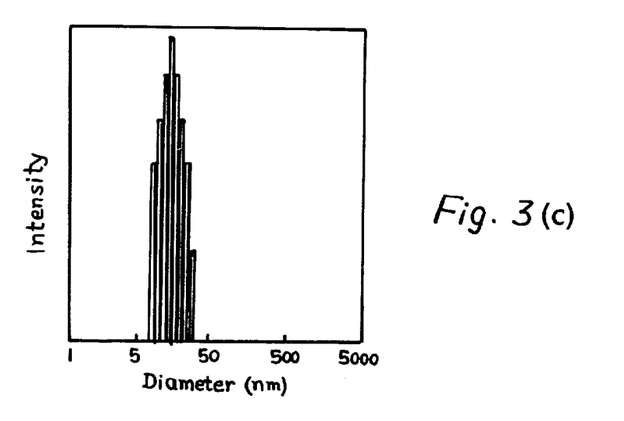
FIG. 3(c) shows nanoparticles made of bovine serum albumin crosslinked with glutaraldhyde.

The size of the drug loaded nanoparticles of polyvinylpyrrolidone, polyethyleneglycolfumarate and bovine serum albumin were determined and representative spectra for each type are shown in the FIG. 3(a) to 3(c):

FIG. 3(a) shows nanoparticles made of polyethylene glycol fumarate containing FITC-Dextran, FIG. 3(b) shows nanoparticles made of polyvinylpyrrolidone containing FITC-Dextran, FIG. 3(c) shows nanoparticles made of bovine serum albumin crosslinked with glutaraldehyde.

The variation of particle sizes changes with the size of the microemulsion droplets. Interestingly the size of the polyvinylpyrrolidone nanoparticles increases exponentially with the increase of droplet size whereas the same remain more or less constant in case of bovine serum albumin-gluteraldehyde particles.

In vitro release kinetic studies

A known amount of lyophilised nanoparticles encapsulating FITC-dextran was suspended in 10 ml of phosphate buffer saline in 50 ml polypropylene tubes. The tubes were placed in water bath maintained at 37 C. At predetermined intervals a volume of 500 ul taken from each tube and was passed through a 100 KD filter (Millipore UFP2THK24) which retained the nanoparticles and the free dye came out in the filtrate. The dye concentration in the filtrate was determined spectrophotometrically.

Figure 4:
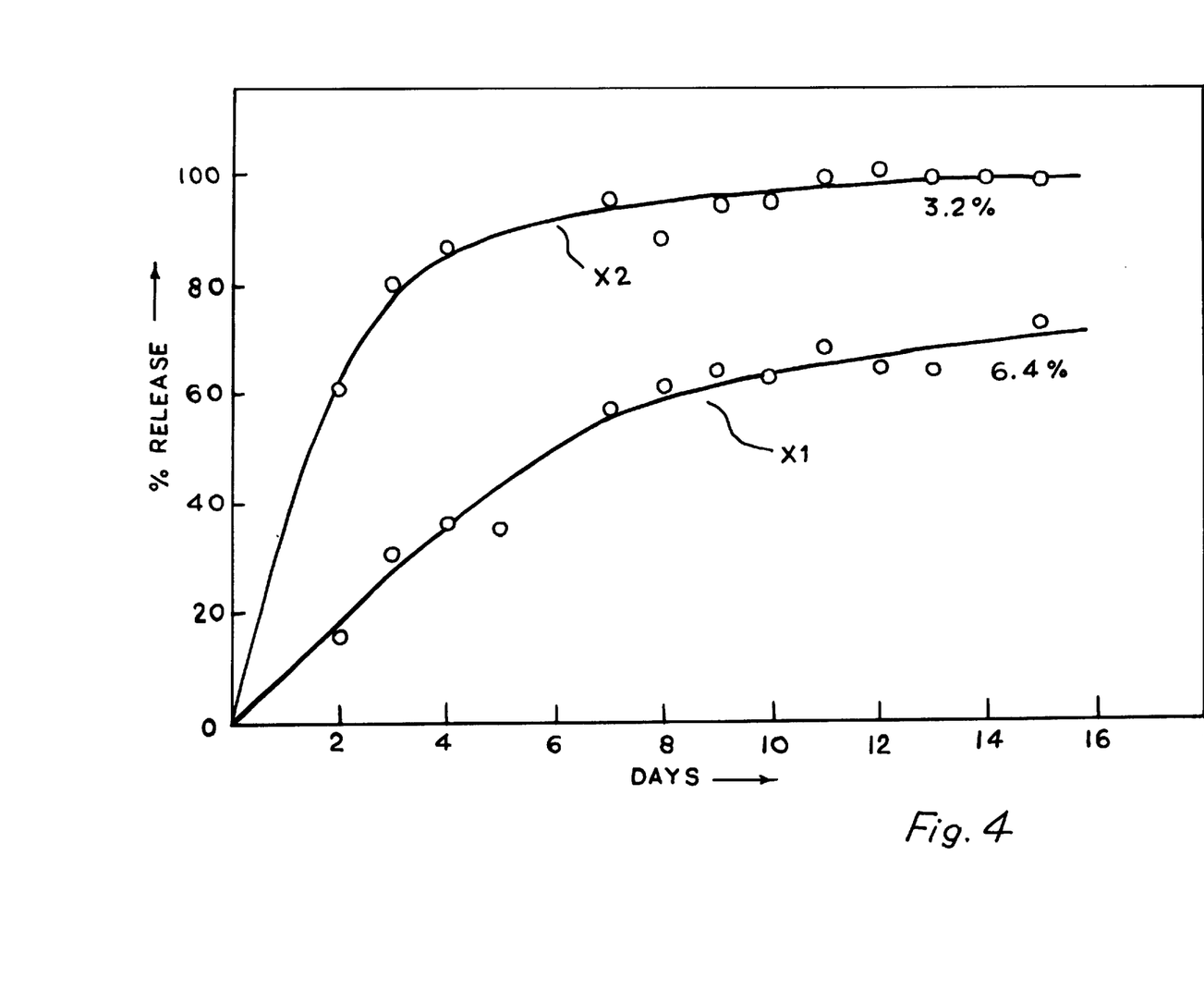
FIG. 4 illustrates the release of FITC-Dextran dye from polyethylene glycolfumarate particles of different loading where curve X1 shows 6.4% loading and curve X2 is 3.2% loading of dye.

The results are shown in FIG. 4, which illustrates the release of FITC-dextran dye from polyethylene glycol fumarate particles of different loading, and where curve X1 shown a 6.4% loading and curve X2 is 3.2% loading of dye.

Figure 5:
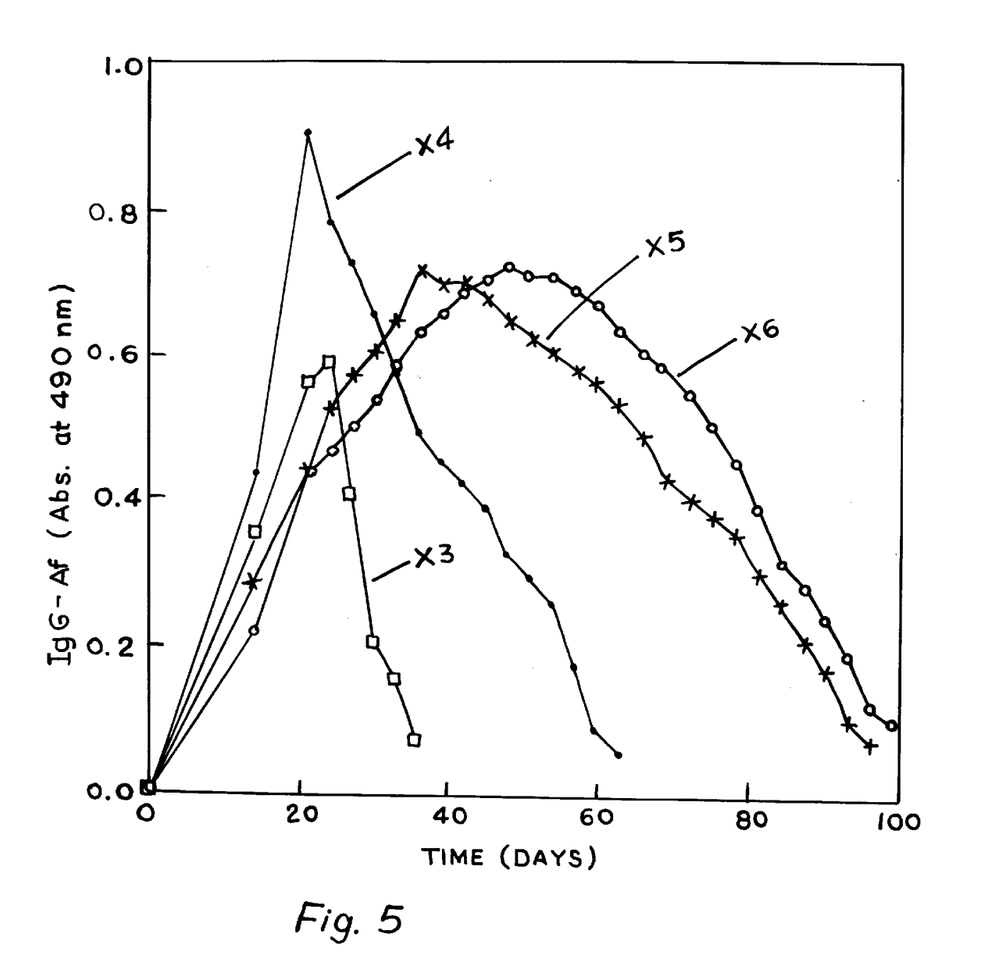
FIG. 5 graphically illustrates the results of an in vivo antibody response in mice serum by injecting antigen encapsulated nanoparticles.

In vivo antibody, response in mice serum by injecting antigen encapsulated nanoparticles. Mice were injected subcutaneously three times at an interval of 7 days with PVP nanoparticles containing 300 ug of Aspergillius fumigatus antigen entrapped in PVP nanoparticles and suspended in 100 ul of normal saline. Each group contains five animals, three of which received the antigen entrapped in nanoparticles, one received free antigen (300 ug) and the controlled received empty nanoparticles suspended in normal slime. Mice were bled at predetermined intervals and the amount of Aspergilus fumigatus specific antibody in the mice serum was assayed using indirect ELISA assay. The results are shown in FIG. 5, which illustrates specific antibody response.

Specific antibody response of antigen of Aspergillus fumigatus entrapped in polyvinylpyrrolidone nanoparticles at different amount of cross linking agent with curves X3, X4, X5 and X6 having 0%, 0.3%, 0.6% and 1.2% of cross linking agent respectively.

We claim:

1. A process for preparing highly monodispersed polymeric hydrophilic biocompatible nontoxic nanoparticles with water soluble biochemical or chemical drugs entrapped therein having a size of from about 10 nm to 100 nm, comprising the steps of:

(i) dissolving a surfactant in oil to obtain unloaded nanoreactor droplets;

(ii) adding aqueous solutions of hydrogel forming monomers or preformed hydrogel forming polymers, selected from the group consisting of vinyl pyrrolidone, mixtures of vinyl pyrrolidone and polyethyleneglycolfumarate, polymers of polyvinylpyrrolidone, copolymers of polyvinylpyrrolidone and polyethyleneglycolfumarate, bovine serum albumins, and additional amounts of hydrogel monomers or hydrogel preformed polymers; monomeric crosslinking agent; an initiator; and a water soluble biochemical or chemical drug to said nanoreactor droplets to obtain a microemulsion which is optically transparent and containing loaded nanoreactor droplets of aqueous core of from 1 to 10 nanometers in diameter;

(iii) subjecting said microemulsion to polymerization to obtain nanoparticles of a size from about 10 to 100 nanometers;

(iv) drying the polymerized reaction product for removal of solvent to obtain dry nanoparticles and other unreacted materials;

(v) dispersing the dry mass in an aqueous buffer; and (vi) separating the surfactant and other toxic materials therefrom.

2. The process as claimed in claim 1 wherein said nanoparticles have a size of 10 nm to 100 nm.

3. The process as claimed in claim 1 wherein said monomers and preformed polymers are biocompatible and nonantigenic materials selected from the group consisting of vinylpyrrolidone, mixtures of vinylpyrrolidone and polyethyleneglycolfumarate, or their polymers selected from the group consisting of polyvinylpyrrolidone or copolymers of polyvinylpyrrolidone and polyethyleneglycolfumarate.

4. The process as claimed in claim 1 wherein said polymers are biocompatible antigenic bovine serum albumins.

5. The process as claimed in claim 1 wherein said cross linking agent is N,N methylene-bis acrylamide (MBA) or glutaraldehyde.

6. The process as claimed in claim 1 wherein the initiators are water soluble perdisulphate salts and the process further comprises an activator which is tetra methyl ethylene diamine (TMED).

7. The process as claimed in claim 1 wherein 1% to 10% of the water soluble biochemical or chemical drug by weight of the polymeric material is encapsulated into said nanoparticles.

8. The process as claimed in claim 1 wherein 0.01M to 0.1M of sodium bis ethyl hexyl sulphosuccinate is used as the surfactant.

9. The process as claimed in claim 1 wherein said oil is an alkane.

10. The process as claimed in claim 1 wherein the dried nanoparticles and surfactant after removing solvent are dispersed in buffer solution and then treated with calcium chloride to quantatively remove the toxic surfactant from the adhering nanoparticles.

11. The process as claimed in claim 1 wherein the nanoparticles dispersed in aqueous buffer are dialyzed to remove the unreacted and toxic materials from the buffer.

12. The process as claimed in claim 1 wherein the dispersed nanoparticles after dialysis are lyophilized and preserved.

13. The process as claimed in claim 1 wherein said microemulsion is a monodispersed optically transparent microemulsion.

14. The process of claim 1 wherein said oil is n-hexane.

* * * * *

UNITED STATES PATENT AND TRADEMARK OFFICE
CERTIFICATE OF CORRECTION

PATENT NO : 5,874,111

DATED : February 23, 1999

INVENTOR(S) : Amarnath MAITRA et al.

It is certified that error appears in the above-identified patent and that said Letters Patent are hereby corrected as shown below:

ON THE TITLE PAGE

[76] line 3, change "Prashant Kumar Ghosh" to --Prasanta Kumar Ghosh--;

line 3-4, change "Block C2B, Flat 5A, Janakpuri, New Delhi-110058" to -- Block C 2/B, Flat No. 5A, Janakpuri, New Delhi-110058.

Signed and Sealed this

Twenty-ninth Day of May, 2001

*Attest:*

NICHOLAS P. GODICI

*Attesting Officer*      *Acting Director of the United States Patent and Trademark Office*